US007491684B2

(12) United States Patent
Narula et al.

(10) Patent No.: US 7,491,684 B2
(45) Date of Patent: Feb. 17, 2009

(54) SUBSTITUTED 3-DECENE-5-ONE/OL DERIVATIVES

(75) Inventors: Anubhav P. S. Narula, Hazlet, NJ (US); Edward Mark Arruda, Cliffwood, NJ (US); Pascal Gaurin, Madison, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 560 days.

(21) Appl. No.: 11/055,146

(22) Filed: Feb. 10, 2005

(65) Prior Publication Data

US 2006/0178291 A1 Aug. 10, 2006

(51) Int. Cl.
*A61Q 13/00* (2006.01)

(52) U.S. Cl. .............................. 510/101; 512/8; 512/25

(58) Field of Classification Search ................. 510/101; 512/8, 25

See application file for complete search history.

(56) References Cited

U.S. PATENT DOCUMENTS

| | | | | |
|---|---|---|---|---|
| 4,169,109 | A * | 9/1979 | Yoshida et al. | 568/313 |
| 4,318,934 | A * | 3/1982 | Boden | 426/534 |
| 4,534,891 | A | 8/1985 | Boden et al. | |
| 4,585,662 | A | 4/1986 | Kaiser et al. | |

OTHER PUBLICATIONS

Fleming, Ian et al: “The alpha. : .gamma. ratios in phenylthiomethlation of silyl dienol ethers”, Tetrahedron Letters, vol. 24, No. 28, pp. 2913-2916, 1983.

Wang, Yong et al: “Formal Intermolecular 4+4 Approach to Cyclooctanoids: 4+3 Capture of the Nazarov Oxyallyl Intermediate with Simple .1,3-Dienes” Organic Letters, vol. 5, No. 15, pp. 2747-2750, 2003.

* cited by examiner

*Primary Examiner*—Gregory E Webb
(74) *Attorney, Agent, or Firm*—Elizabeth M. Quirk; XuFan Tseng; Joseph F. Leightner

(57) ABSTRACT

The present invention is directed to novel ketone and alcohol compounds and the use of these novel compounds in creating fragrances, and scents in items such as perfumes, colognes and personal care products.

7 Claims, No Drawings

SUBSTITUTED 3-DECENE-5-ONE/OL DERIVATIVES

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel compounds, represented by the general structures of Formula I and Formula II set forth below:

Formula I

Formula II

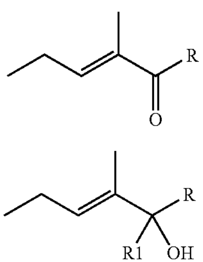

wherein R is a hydrocarbon moiety consisting of 2 to 10 carbon atoms, including cyclopentyl, cyclohexyl, phenyl, benzyl, or phenylethyl. R1 is either methyl or ethyl.

Another embodiment of the invention is a method for enhancing a perfume by incorporating an olfactory acceptable amount of the compounds provided above.

These and other embodiments of the present invention will be apparent by reading the following specification.

DETAILED DESCRIPTION OF THE INVENTION

In Formula I and Formula II above, R represents a hydrocarbon, a cyclic, or an aromatic group consisting of 2 to 10 carbon atoms, most preferably, R is a pentyl group. Hydrocarbon, cyclic or aromatic R groups include, but are not limited to the straight alkyl, cyclic, and aromatic chains. Suitable straight hydrocarbon moieties include ethyl, propyl, butyl, cyclopentyl, cyclohexyl, and the like. Suitable branched hydrocarbon moieties include isopropyl, sec-butyl, tert-butyl, 2-ethyl-propyl, and the like. Suitable hydrocarbon moieties containing double and triple bonds include ethene, propene, 1-butene, 2-butene, penta-1-3-deine, hepta-1,3,5-triene, butyne, hex-1-yne and the like. Suitable aromatic moieties include phenyl, benzyl, phenylethyl and the like. In Formula II above, R1 represents a methyl or an ethyl group. Those with skill in the art will recognize that the compound of Formula I of the present invention has a chiral center, thereby providing several isomers of the claimed compound. As used herein the compounds described herein include the isomeric mixtures of the compounds as well as those isomers that may be separated using techniques known to those with skill in the art. Suitable separation techniques include chromatography, particularly gel chromatography.

The compounds of the present invention may be prepared from the following compound of Formula III:

Formula III

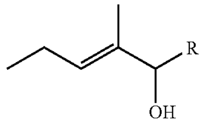

The preparation and use of the compound of Formula III is discussed in U.S. Pat. No. 4,585,662, the contents of which are incorporated herein by reference. In the Formula III, R has the same definition as set forth above.

The compound of Formula I may be prepared from the compound of Formula III by following the Oppenauer oxidation reaction procedure (see Example A). The amount of ketone recovered after the reaction is completed is from about 70% to about 95% by weight of the product mixture. We have discovered that the compounds of Formula I have green, pleasant notes that are well suited for use as a fragrance ingredeint.

The compound of Formula II may be prepared by nucleophilic addition of an appropriately substituted alkyl, cyclic or aromatic Grignard reagent or alkyl lithilum to the compound of Formula I (see Example C). We have discovered that the compounds of Formula II have a banana fruity note with violet, soft green tones that are well suited for use as a fragrance ingredient.

The use of the compound of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. IFF as used in the examples is understood to mean International Flavors & Fragrances Inc.

EXAMPLE A

Preparation of 4-methyl-3-decene-5-one

To a dry 2 liter multi-neck round bottom flask fitted with an air stirrer, nitrogen inlet condenser and an addition funnel 208 g of a 98% solution of Aluminum Isopropyloxide and 400 g of acetone (obtained from the Acros Organics) was added. The resulting mixture was stirred and gently heated. As the temperature of the mixture reached 64° C., 378 g of 90% solution of 3-decene-4-methyl-5-ol was slowly added over 90 minutes. The resulting mixture was aged for 90 minutes. At this point the temperature reached 80° C. and a first sample of the product was taken. Two hours later, as the temperature reached 85° C., a second sample was taken. The mixture was maintained at a constant temperature of 85° C. for 35 minutes, the heating source was removed and 100 ml of acetone was added. After 25 minutes, as the mixture reached 80° C., the mixture was cooled and quenched with 1 L of 10% hydrochloric acid. The products were allowed to settle. Then the organic layer was separated from the acid layer, washed with water and neutralized with 10% $NaHCO_3$ solution.

The NMR spectrum of the 4-methyl-3-decene-5-one is as follows: 0.88 ppm (m, 3H); 0.96 ppm (m 3H); 1.39 ppm (m, 2H); 1.51 ppm (m, 2H); 1.82 ppm (s 3H); 2.21 ppm (m, 2H); 2.71 ppm (m, 2H); 6.27 ppm (m, 1H)

EXAMPLE B

Incorporation of 4-methyl-3-decene-5-one into a Fragrance Formulation

A fragrance was prepared according to the following formulation:

| Material | Parts |
|---|---|
| TRIPLAL EXTRA | 1.00 |
| AMBROXAN DIST | 10.00 |
| AMYL SALT | 5.00 |
| GERANIUM EGYPT SPECIAL | 4.00 |
| METH OCTIN CARBONATE 10% DPG | 2.00 |
| METH IONONE BETA COEUR | 10.00 |
| TIMBEROL DRAG | 5.00 |
| TONALID | 50.00 |
| ISO E SUPER | 100.00 |
| IONONE BETA EXTRA | 8.00 |
| ISO GAMMA SUPER | 40.00 |
| LYRAL | 50.00 |
| MANDARIN OIL YELLOW GATTO | 30.00 |
| POLYSANTOL (ELINCS) | 5.00 |
| VERAMOSS | 5.00 |
| ANETHOLE USP | 1.00 |
| PATCHOULI INDONESIA MD REF A LMR | 2.00 |
| PEACH ALD COEUR SPECIAL 10% DPG | 0.50 |
| LIFFAROME "PFG" 10% DPG | 7.00 |
| COUMARIN | 5.00 |
| ORANGE OIL SWEET GUINEA PECT + BHA | 35.00 |
| BERGAMOT OIL DEFUROCOUMARINIZED GATTO | 42.00 |
| FLORHYDRAL (ELINCS) | 0.50 |
| HEXENYL ACET, CIS-3 | 1.00 |
| ETH LINALOOL HLR | 45.00 |
| ADOXAL | 0.50 |
| STYRALYL ACET | 2.00 |
| SANJINOL | 50.00 |
| LAVANDIN SUPREME CHAU | 8.00 |
| DIHYDRO MYCENOL | 60.00 |
| ROSEMARRY FRENCH VILLECROZE | 1.00 |
| ALLYL AMYL GLYCOLATE | 5.00 |
| HELIONAL | 15.00 |
| CANTHOXAL | 15.00 |
| CYCLOGALBANATE | 3.00 |
| FLORALOZOLE | 5.00 |
| LILIAL | 50.00 |
| NONADIENAL, 2-TR-6-CIS-"F + F" 0.1% DEP | 6.00 |
| RHODINOL COEUR | 9.00 |
| GALAXOLIDE BENZ SAL 50 PCT | 250.00 |
| SANDAL WOOD RECO 2004 YC-973 | 15.00 |
| GALBASCONE 1% DPG | 5.00 |
| MANDARINAL 32048 SAE | 3.00 |
| DAMAROSE | 0.50 |
| CARVONE SPECIAL L-10% DPG | 8.00 |
| AURANTIOL GIV 10% DPG | 6.00 |
| SAGE CLARY FRENCH OIL REF A LMR | 4.00 |
| HEXENYL SAL, CIS-3 | 15.00 |
| AMBREINE PURE 181400/3 BROWN 1% DEP | 3.00 |
| 3-DECENE-4-METHYL-5-ONE | 5.00 |

The above fragrance was found to be a pleasing fragrance with pleasing green notes. The above fragrance formulation was presented to demonstrate the effectiveness of the compounds of the present invention was enhancing, improving or modifying the performance of the formulations in which they are incorporated.

EXAMPLE C

Preparation of 4.5-Dimethyl-3-decene-5-ol

To a dry 5 liter multi-neck round bottom flask fitted with an air stirrer, nitrogen inlet condenser and an addition funnel 1.617 g of $CH_3Li$ was added and stirred. 336 g of 4-methyl-3-decene-5-one (see example A for preparation of 3-decene-4-methyl-5-one) was added dropwise over 105 minutes. The temperature of the reaction rose to 63° C. The reaction mixture was aged for 150 minutes and a first sample was taken at 37° C. 30 minutes later, a second sample was taken at 30° C. The mixture was quenched with acetic acid, allowed to settle and layers separated. The aqueous layer was washed twice with 100 ml of toluene. The toluene extracts were added to the organic layer and washed with $Na_2CO_3$.

The NMR spectrum of the 4.5-Dimethyl-3-decene-5-ol is as follows: 0.88 ppm (t, 3H); 0.94 ppm (t, 3H); 1.28 ppm (s, 3H); 1.15-1.35 ppm (m, 6H); 1.50 ppm (s, 1H); 1.55 ppm (s,1H), 2.05 ppm (m, 2H); ; 5.45 ppm (m, 1 H)

The IR spectrum of the 4.5-Dimethyl-3-decene-5-ol is as follows: OH-stretch broad at 3416 $cm^{-1}$, CH-stretch saturated at 2960, 2933, 2872 $cm^{-1}$, double bond stretch at 1680 $cm^{-1}$, 1462 and 1372 due to CH stretch.

EXAMPLE D

Preparation of Alpha-[1-Methyl-1-Butenyl]-Cyclopentanemetanol

To a dry 2 liter multi-neck round bottom flask fitted with an air stirrer, nitrogen inlet condenser and an addition funnel 800 ml of 2 M of cyclopentyl magnesium chloride was added and stirred. 139 g of 2-methyl-2-pentenal was added over the next 90 minutes. The reaction mixture was aged for another 90 minutes and the first sample was taken. 25 minutes later the reaction mixture was quenched with water, aged for 30 minutes and the organic layer was separated and washed with 2 one liter portions of water.

The NMR spectrum of the Alpha-[1-Methyl-1-Butenyl]-Cyclopentanemetanol is as follows: 1.00 ppm (s, 3H); 1.1-1.2 ppm (s, 1H); 1.4-1.5 ppm (s, 2H); 1.5-1.7 ppm (m, 4H); 1.8 ppm (s, 1H); 2.1 ppm (m, 3H); 3.7 ppm (d, 1H); 5.4 ppm (t, 1H)

EXAMPLE E

Preparation of 1-Phenyl-4-Methyl-4-Hepten-3-one

To a dry 2 liter multi-neck round bottom flask fitted with an air stirrer, nitrogen inlet condenser and an addition funnel 168 g of 65% 1-Phenyl-4-Methyl-4-Hepten-3-ol, 51 g of 98% Aluminum Isopropoxide, (obtained from the Acros Organics) and 200 g of Acetone and 200 g of Toluene were added and stirred. The reaction mixture was slowly heated at reflux to 85° C. The samples were collected every our when the temperature of the reaction mixture was between 70° C. and 80° C.

The NMR spectrum of the 1-Phenyl-4-Methyl-4-Hepten-3-one is as follows: 1.0 ppm (t, 3H); 1.8 ppm (s, 3H); 2.2 ppm (m, 2H); 2.9-3.0 ppm (m, 2H); 6.6 ppm (t, 1H) 7.2 ppm (m, 3H); 7.28 ppm (s,1H), 7.3 ppm (s, 1H).

EXAMPLE F

Preparation of 1-cyclohexyl-2-methyl-2-penten-1-ol

To a dry 2 liter multi-neck round bottom flask fitted with an air stirrer, nitrogen inlet condenser and an addition funnel 800 ml of 2 M of cyclohexyl magnesium chloride was added and stirred. The flask was cooled to 10° C. 146 g of 99% 2-methyl-2-pentenal was added over the next 135 minutes. The cooling was removed. The first sample was taken 50 minutes later at 13° C. The second sample was taken 35 minutes later at 18° C. 75 minutes later the reaction mixture was quenched with 1000 ml of 20% HAc with cooling. The layers were allowed to settle and the organic layer extracted with 100 ml of toluene.

The NMR spectrum of the 1-cyclohexyl-2-methyl-2-penten-1-ol is as follows . . . 0.7-0.9 ppm (q, 1H); 0.9-1.0 ppm (t, 4H); 1.1-1.3 ppm (m, 3H); 1.6 ppm (s, 3H); 1.6-1.8 ppm (m, 4H); 2.0-2.1 ppm (m, 3H); 3.7 ppm (d, 1H); 5.4 ppm (t, 1H)

What is claimed is:

1. A compound 4-methyl-3-decene-5-one.

2. A method of improving, enhancing or modifying a fragrance formulation through the addition of an olfactory acceptable amount of the compound of claim 1.

3. The method of claim 2 wherein the fragrance is incorporated into a product selected from perfumes, colognes, toilet waters, cosmetic products, personal care products, fabric care products, cleaning products and air fresheners.

4. The method of claim 3 wherein the cleaning product is selected from the group consisting of detergents, dishwashing compositions, scrubbing compounds and window cleaners.

5. The method of claim 2, wherein the amount incorporated into a fragrance is from about 0.005 to about 10 weight percent.

6. The method of claim 2, wherein the amount incorporated into a fragrance is from about 0.5 to about 8 weight percent.

7. The method of claim 2, wherein the amount of incorporated into a fragrance is from about 1 to about 7 weight percent.

* * * * *